United States Patent [19]
Horwitz

[11] Patent Number: 5,963,300
[45] Date of Patent: Oct. 5, 1999

[54] OCULAR BIOMETER

[75] Inventor: Larry S. Horwitz, Seal Beach, Calif.

[73] Assignee: AMT Technologies, Corp., Pacific Palisades, Calif.

[21] Appl. No.: 09/024,842

[22] Filed: Feb. 17, 1998

[51] Int. Cl.⁶ ..................................................... A61B 3/14
[52] U.S. Cl. .......................................... 351/209; 351/212
[58] Field of Search ..................................... 351/205, 206, 351/207, 209, 210, 211, 212, 246, 247; 356/359, 376

[56] References Cited

U.S. PATENT DOCUMENTS

| | | |
|---|---|---|
| 4,125,430 | 11/1978 | Rassow . |
| 4,173,398 | 11/1979 | Okamoto . |
| 4,293,198 | 10/1981 | Kohayakawa . |
| 4,353,625 | 10/1982 | Nohda . |
| 4,372,655 | 2/1983 | Matsumura . |
| 4,376,573 | 3/1983 | Matsumura . |
| 4,390,255 | 6/1983 | Nohda . |
| 4,421,391 | 12/1983 | Matsumura . |
| 4,459,027 | 7/1984 | Kafri . |
| 4,640,596 | 2/1987 | Humphrey . |
| 4,650,301 | 3/1987 | Humpnrey . |
| 4,669,835 | 6/1987 | Humphrey . |
| 4,730,917 | 3/1988 | Krueger . |
| 5,157,427 | 10/1992 | Humphrey . |
| 5,164,750 | 11/1992 | Adachi ..................................... 351/212 |
| 5,208,619 | 5/1993 | Campbell . |
| 5,223,863 | 6/1993 | Heine . |
| 5,252,999 | 10/1993 | Sukigara . |
| 5,258,791 | 11/1993 | Penney . |
| 5,270,749 | 12/1993 | Okamura . |
| 5,576,780 | 11/1996 | Yancey . |

Primary Examiner—George Manuel
Attorney, Agent, or Firm—Sanford Astor

[57] ABSTRACT

An ocular biometer utilizing a light emitting source (7) and corresponding optics to illuminate areas of the eye in order to analyze the wavefront of the reflected light. Aperture sharing elements, such as "hot mirrors" (4) are used to allow the eyes (1) to view the world, as the ocular biometer measures various characteristics of the eye such as the refractive (i.e., accommodative) state, the gaze angle and the pupil diameter at any instant of time and continuously. Optical wavefront conditioning and wavefront sensing techniques are used to determine the refractive power of the eye and the instantaneous accommodative state. Reflected light is projected through a reticle (26) or plurality of reticles (26, 28). Spatial characteristics of the resulting shadow pattern uniquely determine the characteristics of the eye. These shadow patterns can be measured directly or by causing a modulation of the lines with a second identical reticle placed appropriately between the first and the imaging plane. The bright pupil and a Purkinje image may be used to compute the gaze angle (or, line-of-sight). A bright pupil on a dark background wil provide the pupil diameter measurement. The ocular biometer can be configured in a binocular manner so that both eyes can be investigated simultaneously for strabismus, stereopsis and convergence measurements. The depth of modulation of the modulated shadow pattern provides an indication of the acuity of the ocular media and the retinal surface thus providing a means for screening such medical anomalies as diabetic retinopathy, glaucoma and cataracts.

42 Claims, 11 Drawing Sheets

OCULAR BIOMETER

BACKGROUND OF THE INVENTION

Improving eyesight is vitally important. Precise measurement of the eye's physical characteristics, such as ocular refractive power, figures of surfaces including features of the eye in order to prescribe vision correction is also vitally important.

Since the Chou Dynasty (circa 479–381 B.C.) man has tried to correct his vision, knowing that the measurement of how much correction is required is a major part of the problem. Typically, in contemporary practice Snellen's charts are used with a phoropter to pragmatically and subjectively quantify the vision correction. This process relies on patient response to quantify the measurement. Auto refractors have been invented that use the knife edge test, myers and other optical principles, to quantify the visual acuity via light reflected from, or imaged on the retina. Optical characteristics of the eye are qualified by specific aberrations.

Currently, patient refraction measurements require verbal feedback from the patient in order to quantify the refraction measurement. Thus, in order to perform the measurement on both eyes simultaneously, the number of independent variables in the concurrent indicators allow too many degrees of freedom and thus there would be no accuracy in the refraction of either eye. Consequently, only one eye can be measured at a time. One of the enabling technologies of this invention is the ability to measure the refractive states, and thus the corrections required in a binocular mode of operation, i.e., both eyes simultaneously.

The technology of this invention is the result of treating the eye as an optical system. The optical train from the vertex of the cornea to the focal plane of the retina can be analyzed with the same fundamental techniques as sophisticated optical systems, that is, by analyzing the optical wavefront that passes through the system. In this invention a method for analyzing such an optical wavefront is disclosed.

A characteristic of the eye is needed in order to track its motion and strabismometry. Methods have been used that scar the cornea and track the scar. Tracking the inside edge of the iris is another technique that has been used, however the iris diameter changes with ambient light and ocular field of regard. Thus, the error induced as the result of iris tracking is larger than the magnitude of the motion measured, leaving it an invalid technique. This invention enables eye tracking by using geometrical characteristics of the entire pupil and a corneal glint to track the eye.

Classical techniques for measuring the quality of optics or optical designs are not suitable for measuring the optical performance of the eyes. A relationship between an impinging beam and the reflecting beam gives information about the eye's characteristics.

A method other than applying interferometry to measure optical characteristics is obtained from allowing light exiting the system to cast the shadow of a reticle. If the physical characteristics of the shadow pattern change are different than expected, the deviations can be analyzed and the anomalies can be quantified. This invention is particularly related to the analysis of light as it exits the eye post reflex from the ocular fovea. This reflex light must be appropriately conditioned, due to the reflective characteristics of the retina, so that it may be spatially coherent enough to provide the shadow conditions.

The method of this invention by which the optical wavefront at the vertex or the cornea is produced and analyzed is a primary feature of this invention. No means exists for accurately determining the optical characteristics of the eye in a continuous, real time and binocular (if desired) fashion. Moreover, Applicant is unaware of any techniques whereby reflections can be obtained from the retina and made to be cooperative, such that more specific measurements such as characteristics of features of the eye (i.e., refractive optical power state, corneal topography, corneal pachymetry, retinal acuity, ocular acuity, pupillometry, etc.) can be determined. More specifically, Applicant is unaware of any known ability to measure and analyze the data from a wavefront sensor. Such usefulness would include automatic evaluation of corrective lenses required for vision, characterization of eye motion and screening for acuity.

Processing the optical wavefront to provide measurement of the optical characteristics of the eye is valuable. This invention also relates to the processing and analysis of optical wavefront data. More specifically, the invention is directed to the optical wavefront containing information concerning characteristics related to the wavefront reflex from the retinal surface or corneal surface. Both optical and software means are used in individual and integrated forms to analyze the optical wavefront. Shadow patterns are produced when the optical wavefront is obscured in its propagation path by the pattern of a reticle such as a Rouchi ruling. These shadow patterns can also be made to produce lower spatial patterns by projecting them onto a second reticle. The resulting pattern is an interaction of two patterns that are near the same frequency, which is the superposition, interaction or interference of two simple harmonic functions that have different frequencies, be they electromagnetic, acoustic or spatial. In classical optics these patterns are know as Talbot interferograms, Fresnel patterns or moires. With such information, valuable refractive characteristics of the eye can be measured.

Fringe patterns are caused by a wave optics interferometric process. In one form of such process, a collimated light beam is divided so that part of the beam is directed towards a reference and another towards a target. Reflections from the reference and target interfere to provide an interferometric pattern. Interpretation of the pattern can provide measurement characteristics about the target. This technique is not applicable to the retinal reflex wavefront from live eyes since the geometrical relationship between the two optical paths must be held constant and spatial coherence must be maintained. This is not possible with a retina that is usually moving.

Another form of interferometric pattern is generated, in this invention, by the interference formed when two transparencies (e.g., grating-like), each with similar or identical regular patterns, overlap. The transmission of light through each transparency creates shadows. The fringe pattern is the shadow that is generated through the superposition of the shadows of the two separated transparencys' shadows. The interpretation of this pattern can provide useful information about geometric characteristics of an optical wavefront as reflected from different ocular interfaces. This is related to the reflection from the retina, the cornea and the endothelium.

The fringe pattern can be distorted by noise in the system generating the pattern. The noise can be electronically generated, caused by the camera and optical system used in the measurement, or by background or spurious light interference. Additionally, different reflectivity characteristics of the surface disassociated with the measurement being sought, can also impact accurate measurement. The reflectivity problems could arise, for instance, where different contrast characteristics of the surface exist. Alternatively, this can be caused by different background sources directed on the surface in a manner unrelated to light associated with the optical measuring system. A method for eliminating noise is provided in this system.

OBJECTS OF THE INVENTION

It is an object of this invention to provide an improved technique and apparatus for an optical wavefront sensor.

In one embodiment, light is used to illuminate the ocular retina. The reflected light propagates through the ocular media, the lens and cornea. Analysis of the optical wavefront outside the cornea provides the refractive power of the eye and thus the distance at which the eye is focused.

A further object of the invention is to provide the measurement as to where the eye(s) is looking in three spatial dimensions for refraction, strabismus and vergence.

A further object of the invention is to provide the refractive correction that is needed to be applied to the eye(s) for vision correction; a refractor, refractometer or autorefractor.

A further object of the invention is to provide the binocular operation and thus binocular vision correction or vision fixation for a binocular refractometer, binocular autorefractor or binocular refractor.

In one embodiment, light is used to illuminate the ocular media as a pupillometer, coreometer or coreoscope. The retinal reflex light is apertured by the pupil of the eye. When the pupil is recorded by an imaging sensor such as a CCD (charge coupled device) camera, the pupil appears bright compared to the rest of the image. By measuring the area of the bright pupil the diameter of the pupil can be derived.

In another embodiment of the invention the eyes are tracked in one, two or three spatial dimensions. The incident illumination of the eye(s) is of a calibrated optical wavefront, preferably plane, so that in the object plane of the imaging system the cornea produces the first Purkinje image which is a glint. The geometric relationship between the first Purkinje image and the centroid of the pupil provides the gaze angle of the eye(s) in the one or two tangential spatial/angular dimensions with respect to the face. The third tracking dimension is the distance away from the face.

Yet another object of the invention is to provide strabismus measurements of the eye(s). The strabismometer measures the gaze (look) angle of the eye(s) and compares it to respective angles of a target at which the eye(s) is tasked to look.

If the gaze angle measurements are made with the two eyes in a binocular mode, the two measurements can provide the ocular convergence ("vergence") measurement. This is the location at which the lines-of-sight of the two eyes meet. This function provides the stereopsis or three dimensional viewing capability of the eyes.

Thus, a further object of the invention is to provide an improved technique and apparatus for measuring the convergence (or vergence) of a sighted creature.

If the eye(s) is provided a means (such as a hot mirror, aperture sharing element, beam combiner) so that the eye(s) is viewing a scene (artificial, superficial, virtual or real), the three spatial/angular measurement functionality of the invention can be used as a control-loop function to provide an image at the appropriate perspective for the eye(s). The eye tracking function can also be used as a monitoring technique in observing or recording the visual or neuro-ophthalmic response of the eye(s).

Thus, another object of the invention is monitoring of the eye(s).

With the illumination convergent, or focused to an intra-corneal position, the illumination reflects from the corneal epithelium and endothelium surfaces. An optical lens placed in the optical path of the illumination provides this focusing effect. The endothelium reflection differs from the epithelium reflection by either spectral or optical polarization characteristics.

The corneal anterior reflection can be directed to the wavefront sensor, the wavefront analyzed, and the topography of the cornea(s) can be analyzed. Thus, another object of this invention is to provide the topography of the corneal surface; a corneal topograph or topographer.

The illumination reflected from the corneal endothelial surface can be directed to the wavefront sensor and the topography of the corneal endothelial surface can be measured. Thus, another object of this invention is to provide the topography of the corneal endothelial surface; a corneal endothelial topograph or topographer.

Upon comparing the anterior and the posterior corneal surfaces, the thickness of the cornea can be determined. Thus, a pachymetry measurement can be made of the cornea. Thus, another object of this invention is to provide the pachymetry of the cornea; a corneal pachymeter or corneal pachytopographer.

SUMMARY OF THE INVENTION

This invention provides a system, apparatus, and method for improved measurement of ocular parameters. Specifically, the invention provides a system for ocular vision analysis whereby in either monocular or binocular modes the refractive state of the eye(s) is (are) measured as well as the line-of-sight of each eye and the pupil response. This information can be used to ascertain where the eyes are looking in three dimensional space for use in vision correction analysis, research or a feedback loop in any system requiring this information.

The measurement of an ocular parameter comprises the generation of a light beam and the direction of that beam toward the eye. The beam is reflected from the retina or the cornea of the eye and is directed through a single reticle (grating) or a plurality of reticles (gratings) that are separated by a known distance to develop a shadow pattern. Analyzing the shadow pattern provides measurement data of a parameter of the eye specifically, the refractive state or corneal topography.

The element to be measured is an anatomical surface or an interface in the eye. Selectively, this maybe the retinal surface and the analysis provides refractive data about the eye and/or acuity of the retina for sight. Where the surface is the epithelial surface the analysis provides topographical data of the cornea, i.e., keratometry or keratopography. Where it is the endothelial surface, the analysis provides, together with the epithelial data, a thickness measurement of the cornea, i.e., pachyimetry.

In a preferred form of the invention, the data is used to assert the refractive state of the eye(s).

In another preferred form of the invention, the data is obtained globally over the corneal surface to assert corneal shape or corneal thickness over the entire surface.

In one preferred form of the invention the data is analyzed to determine movement (rotation or translation) of anatomical features of the eye or the cornea.

In other preferred forms of the invention, collimated beams at selected wavelengths are directed to different ocular surfaces and respective fringe patterns are obtained and analyzed. Preferably, the data for each surface is collectively analyzed. This gives information and overall parameters of the particular ocular surface and the physiology defined by the surface.

Also according to the invention, there is provided means for receiving data representative of a predetermined fringe pattern, where that pattern is representative of the measurement characteristics as applied to correlations techniques in pattern data processing.

In a preferred form of the invention, the measurement characteristic is the retinal surface characteristics of the eye and the topography of the epithelial surface and endothelial surface of the cornea. With this information, refractive and diffractive characteristics of the eye are obtained. This will permit correction by prosthetic devices such as eyeglasses or contact lenses or by treatment of the eye with laser-directed power.

In a further preferred form of the invention, the fringe pattern is a Talbot interferogram or shadow pattern and is analyzed in order to extract data related to the metrology of the object. The analysis means is a technique disclosed herein. The shadow pattern is a set of curvalinear lines that in the spatial frequency domain have unique characteristics. The characteristics can be used to specifically analyze the electromagnetic wavefront. Analysis of the refractive power of the eye, shape of the cornea and shape of the endothelial surface of the cornea is extracted by determining the location of the central frequency in the pattern and the higher order frequencies in orthogonal space. The magnitude and phase of the spatial frequency components provides the magnitude and orientation of the spatial modes, i.e., focus, astigmatism, third order and higher, existing in the optical wavefront or polytonic surface.

The shadow projection technique used in this invention allows for adjustable sensitivity of measurement and insensitivity to motion of the eye to allow high quality, quantified ocular aberrations to be measured without patient response. Near infrared energy in the 780 to 900 nanometer spectral range has a high reflection coefficient in the choriocapillaris and pigmented epithelium of the retina. If the laser beam is well conditioned when it enters the eye, the reflected wavefront can be analyzed to measure many aberrations of the eye.

In a preferred form of the invention, the stabismic characteristics of the eye(s) is measured and quantified in the form of a strabismometer (also known as ophthalmotropometer or strabometer). The optical axes of the eyes are determined and the vergence condition measured and quantified.

Other features of the invention are now further described with reference to the accompanying drawings and detailed description.

DETAILED DESCRIPTION OF THE INVENTION

Figure 1:
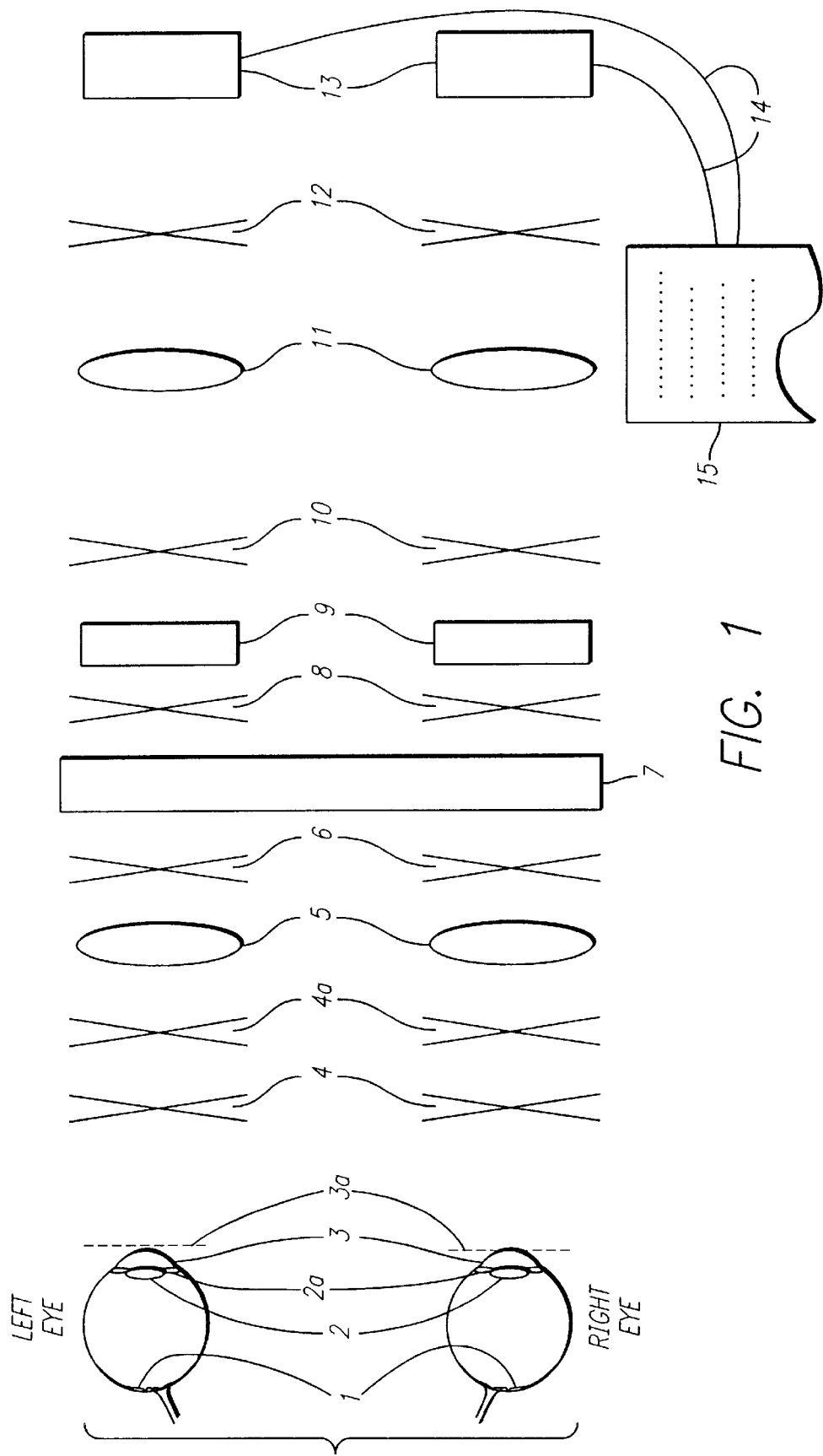
FIG. 1 is a schematic diagram of the system in accordance with the present invention, for automatic measurement of the refractive power of the eyes in a monocular or binocular mode, as well as the pupil diameter and gaze angle.

The refractions of both eyes of the patient are measured simultaneously as the patient views real objects through a viewing port. As the refractive state changes, the ocular biometer of this invention provides measurements in real time so that the physiological transients of accommodation can be observed. Concurrently, the pupil size is observed and directions of the lines-of-sight are observed (i.e., eye tracking). With the same technology, the shape and thickness of the cornea are measured continuously throughout the entire extent of the cornea. These measurements are made at the frame rate of the video camera in the system. Necessary vision correction via refraction, strabismus or neural response can be ascertained via the technology disclosed.

After a period of measurement the data is manipulated and the complete optical characteristics of both eyes are known. Simultaneous far field and near field optimization are performed in order to optimize the optical capability in both fields and all intermediate points.

The ocular biometer measures the optical wavefronts reflected from the retina and corneal surface (with adjunct optics). Spectral reflectance characteristics of these surfaces allow the segregation of the wavefronts so that all optical characterizations can be measured. The spectral reflection peaks are as follows:

Corneal epithelial surface: near infrared, visible and uv spectra

Retinal surface: 780 to 900 nm.

An infrared (780 to 900 nanometer) beam is directed into the eye. It is focused by the corneal media and by the lens, optically scattered from the retina, and then exits the eye through the lens and cornea. Wavefront analysis is performed by passing the optical wavefront through an optical relay system then through one or a multiplicity of reticles that are arranged parallel, in planes normal to the direction of propagation and rotated with respect to each other in those planes. The resulting shadow pattern is imaged on a matte screen and then recorded by a video camera. The recorded image is processed via spatial frequency domain characterization techniques in order to derive the shape of the wavefront exiting the eye. This wavefront contains all of the information concerning the aberrations in the optical system of the eye. With the spatial characteristics known, the wavefront is then fit to the well understood aberrations, e.g. focus and astigmatism. Now the optical aberrations of the eye are defined precisely.

By fixing the gaze of the eye in one direction and moving the biometer off-axis still directed toward the cornea and pupil, one can assess the Spatially Resolved Refraction (SRR) of the eye. Thus, the ocular biometer can provide the refraction of the eye both along the line-of-sight and transverse to it.

Since the shadow pattern produced moves with the eye, it can be tracked to qualify and quantify the motion of the eye. Simple eye motion can be characterized by tracking the transverse plane and area tracking in the axial direction. Detailed eye motion tracking is achieved by this technique, integrated with the actual analysis of the shadow pattern. This eye dynamics sensor is used to track the motions of the eyes during this entire procedure in a monocular or binocular form. The subsystem of this invention in the binocular form can be used as a strabismometer, also known as ophthalmotropometer and strabometer for measurement of the vergent visual axes of the eyes; in Helmet Mounted Display (HMD) systems for fine pointing and tracking mechanisms; as a mental alertness indicator that is characterized by eye motion (sporadic or intentioned) used to detect falling asleep, drug usage or alcohol usage, i.e., sobriety; video games where eye motion is an interaction with the game; and in research where eye motion is a parameter.

DETAILED DESCRIPTION OF THE DRAWINGS

Figure 2:
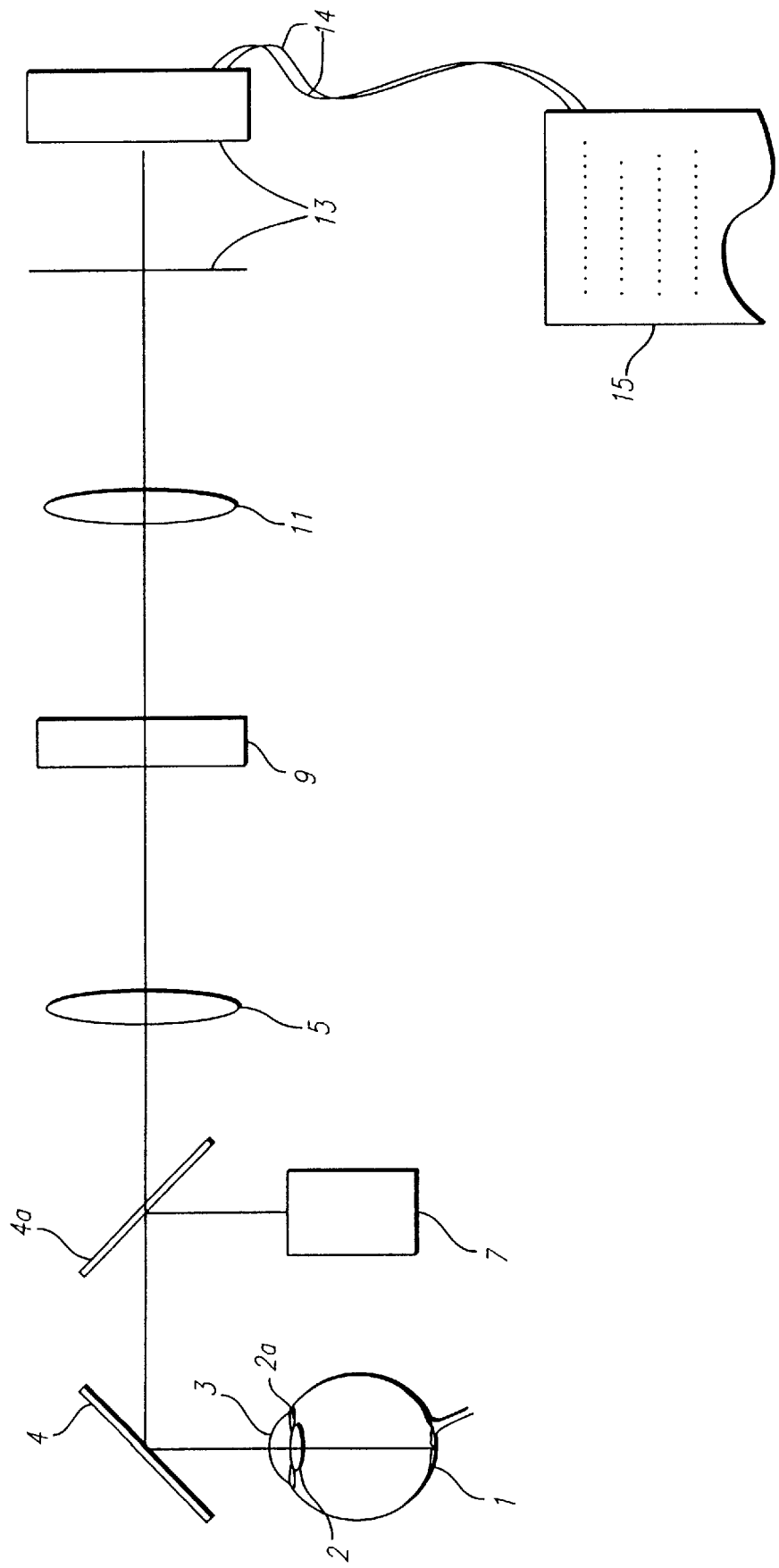
FIG. 2 is a schematic of a particular monocular configuration of FIG. 1.

FIG. 1 and FIG. 2 schematically show the ocular biometer of this invention. The binocular configuration can be split into two monocular systems thereby proceeding with one eye at a time. The subject eyes 1 look thru the system via a "hot mirror" 4 which may also be known as an aperture sharing element. It allows the visible spectrum to transmit through element 4 and specific radiation in the infrared spectrum (780 to 900 nanometers (nm)) to be reflected. The subject is told to watch moving objects in a scene and thus the subject is adjusting his or her focusing field over a wide range. Elements 3a thru 13, of FIG. 1 are arranged with respect to the specific application of the ocular biometer, e.g., helmet or visor mounted, hand held instrument, bench mounted system, etc. Element 4a is also an aperture sharing element, which shares the optical path of the eye refracted wavefront with an illumination source 7. Element 4a is a beam splitter that allows a portion of the light to pass through and the rest of the light to be reflected from illumination source 7. Elements 3a, 5, 11 and 13 comprise a relay lens arrangement. The specific design may require that this configuration produce magnification from the object plane 3a to the data image plane at 13. The configuration may vary depending upon the results desired.

In FIG. 1 elements 6, 8, 10, and 12 are optical steering mirrors or beam splitters (i.e., aperture sharing elements) which may or may not exist in a specific design. They are used to vary the specific design according to the configuration requirements but have no consequence on the wavefront sensing phenomenology, other than radiant optical power distribution. The eyes 1 are illuminated by illumination source 7 which may be a laser, light emitting diode or any light source that has in its spectrum, infrared, visible and ultraviolet.

The objective of the optical system within 7, 6, 5, 4 to 3a is to produce a calibrated, preferably planar, optical wavefront at the 3a position. If tracking the eye(s) is a function of the ocular biometer, this wavefront must be well understood. It is important that the cornea 3 are in near proximity of the 3a object plane. The curved surface of the cornea 3 that is impinged by the wavefront, produces a glint which will be imaged by wavefront sensor 13 and is a critical element of the eye tracking function of the ocular biometer.

In the refractive state measurement of the biometer, though it is preferred, it is not necessary to have a planar wavefront impingent on the eye(s). The optical energy is refracted by the cornea 3 and the lens 2, then is incident on the retina(e) 1. Each rod and cone in the retina becomes a point source as they reflect the incident infrared (IR) illumination. The reflected light is apertured by pupil 2a. An IR camera/sensor contained in wavefront sensor 13, as shown more specifically in FIG. 3, item 32, detects a bright pupil on a dark background. The geometrical centroid of pupil 2a is the second data point that provides the eye tracking algorithm. The reflected light is refracted by lens 2 and cornea 3 so that the wavefront at the optical axial corneal vertex (plane 3a) contains the entire status of the refractive characteristics of the eye. The relay lens system then transfers this wavefront to the wavefront sensor 13 as described in FIG. 3. However, the wavefront at plane 3a is the accumulation of all of the wavefronts from each of the retinal reflection. Each has all of the refractive information about the eye. Unfortunately, when they are added together at the vertex of the cornea there is no discernable information. Thus, the wavefront needs to be conditioned before it gets to the wavefront sensor. The point sources are spatially displaced. Thus, in the Fourier plane 9 of the relay assembly the point spread functions of each of the point sources is spatially displaced. Therefore, a wavefront conditioning baffle assembly 9 is placed in the Fourier plane (i.e., the distances from 3a to 5 and from 9 to 5 are the focal length of lens 5.) Finally, at wavefront sensor 13 the wavefront is analyzed to provide the refractive state of the eyes. This information alone is useful. However, if compared to the reference distance at which the eye is trying to accommodate, the vision correction can be determined. The eye tracking, refractive and pupil size data is determined by the computer in wavefront sensor 13, seen in more detail in FIG. 3, and communicated 14 to an output device 15. All of these parameters are correlated to the ability of the ocular biometer to accurately determine the state of refraction, pupilometry and strabismometry of the subject eye(s) displayed at output device 15.

An example of a particular monocular configuration of the optical schematic of FIG. 1 is illustrated in FIG. 2. The illumination is collimated in illumination source 7. It propagates to aperture sharing element 4a and partially reflected (the remainder of the light is transmitted through the element). As the eye 1 gazes through aperture sharing element 4, the illumination reflects from it and is incident upon and transmitted into the eye 1. The scattered light from the cornea 3 is imaged by the camera in wavefront sensor 13. The illumination that enters the eye is reflected from the retina 1. This reflex light propagates through the lens 2, is apertured by the ocular pupil 2a and propagates through the cornea 3. The optical wavefront reflects from aperture sharing element 4, partially passes through aperture sharing element 4a and is focused in the region of spatial baffle 9. Baffle 9 eliminates undesirable data whereupon lens 11 re-images the wavefront at the analyzer 13. The desired data is transmitted via interlink 14 to output device 15.

Figure 3:
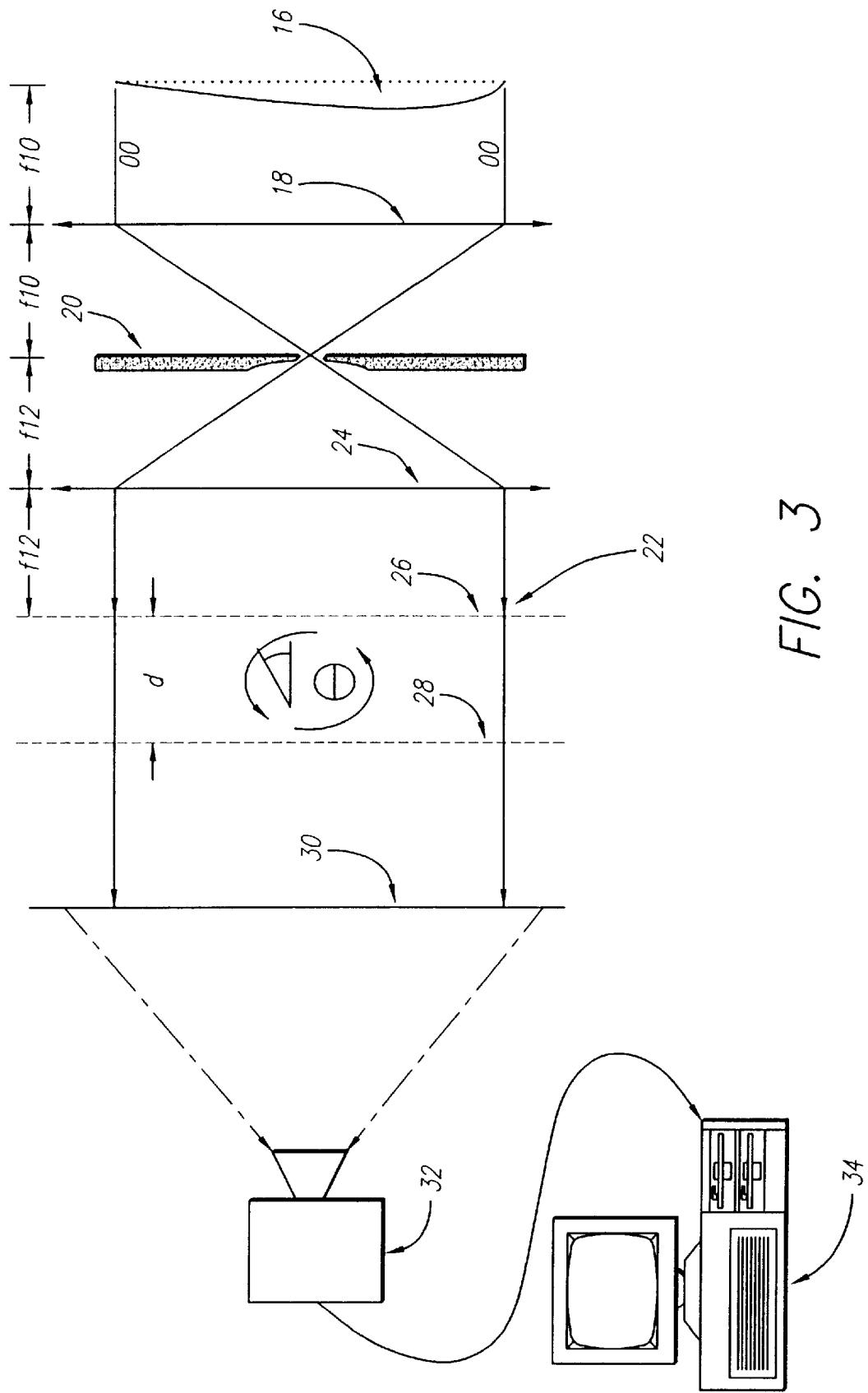
FIG. 3 is a diagram of the optical wavefront sensor technique for the analysis of the wavefront reflected from the respective ocular surfaces.

Wavefront sensor 13 is schematically illustrated in more detail in FIG. 3. The wavefront to be measured 16 enters the sensor and passes through lens 18 of focal length f10 and is focused in the region of spatial baffle 20. The wavefronts that are not eliminated are reformed in plane 22 by lens 24 which has focal length f12. At plane 22 there is one reticle 26 or two reticles 26 and 28. The single reticle 26 is placed a distance d from a matte screen 30.

The pair of reticles 26 and 28 are in parallel planes that are azimuthally rotated through an angle θ with respect to each other and axially displace a distance d. In the single reticle system, a shadow pattern is produced by the wavefront projecting shadows of reticle 26 onto matte screen 30. By comparing the spatial frequencies of the shadow pattern to the reticle, the characteristics of the wavefront can be ascertained and thus the refractive status of the eye determined.

With the dual reticle system the gratings are preferably identical, but not necessarily. The shadow pattern from reticle 26 caused by wavefront 16 is projected onto reticle 28 producing a shadow pattern 30, which is representative of the first derivative of the wavefront. The shadow pattern 30 is recorded by an image recording device 32 that is sensitive in the IR region of the illumination, such as a CCD (charge couple device) camera. If the incoming wavefront is as referenced and unperturbed (plane wavefront) (dotted line) at 16, the result will be a shadow pattern that is periodic bright and dark straight fringes. When there is aberration in the wavefront as in 16 (solid line), the resulting shadow pattern will be perturbed as compared to the shadow pattern as result of a plane wavefront. The perturbation will be in angular orientation and/or spatial curvature of the fringes. Computer 34 is then used to analyze the wavefront.

Figure 4:
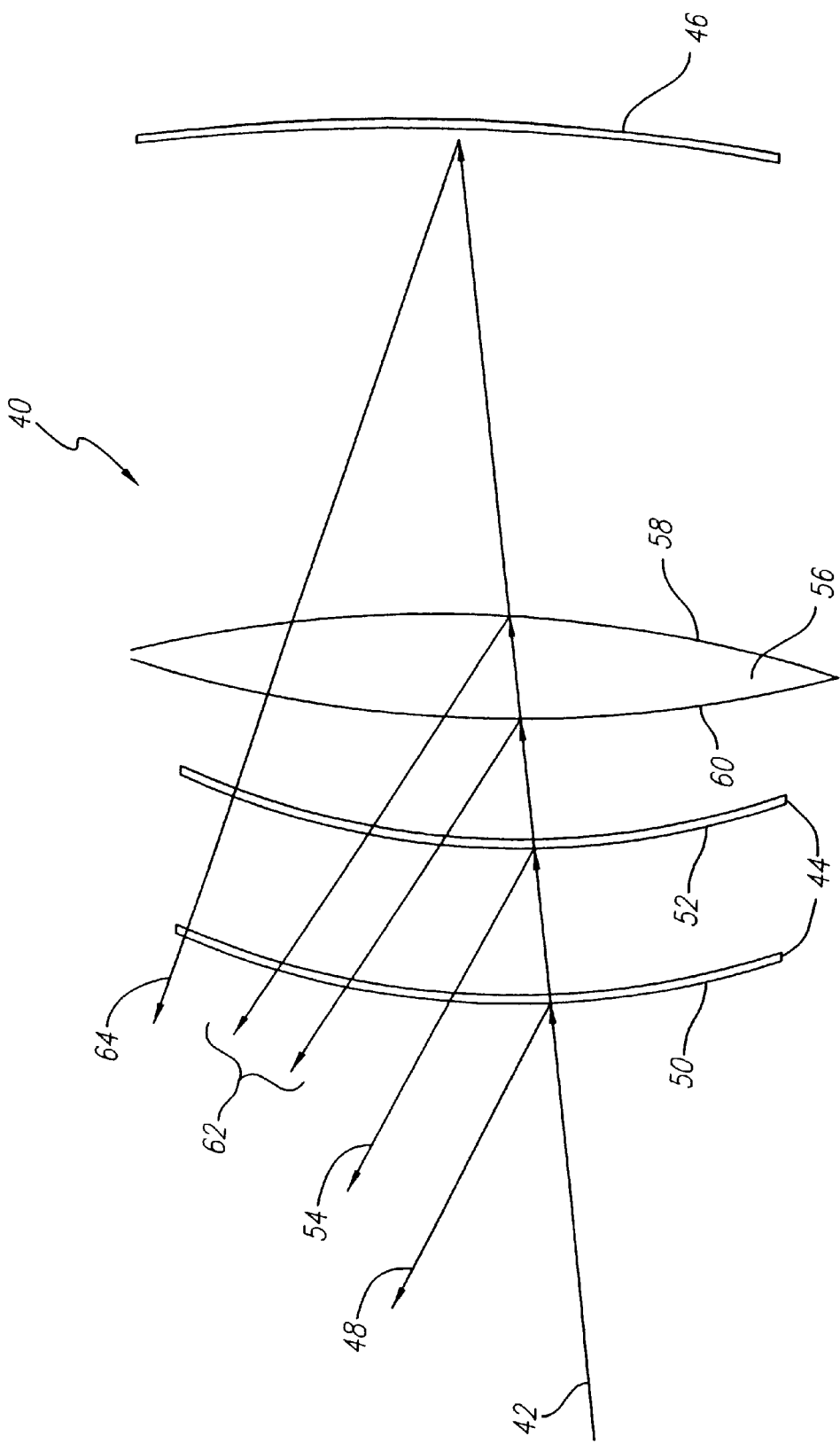
FIG. 4 is a diagram of the spectral reflectance characteristics of the ocular surfaces in the spectral-biometers.

In FIG. 4 the spectral reflectance characteristics of the eye 40 are illustrated. Assuming a wide spectral band white light source 42 illuminating eye 40, predominant spectral region of the light will be reflected from each surface of eye 40. The cornea 3 has two surfaces of interest and the retina 46 provides the reflection for the optical system sampling wavefront. Though there is specular reflection at each surface there is a spectral response embedded in each reflection. Thus, at each surface there is a different "color" reflected. Spectral reflection 48 from the anterior epithelial corneal surface 50 is the very wide spectrum for the IR, through the visible spectrum and ultraviolet. Descemet's membrane and the endothelial are at the back surface 52 of cornea 44. Peak spectral specular reflectance 54 from this surface 52 occurs nominally in the 525 nanometer region. The lens 56 has two surfaces 58 and 60 which can reflect energy 62 in the yellow spectral region. Finally, retina 46 reflects 64 very strongly in the 780 to 900 nanometer optical wavelength region.

Figure 5:
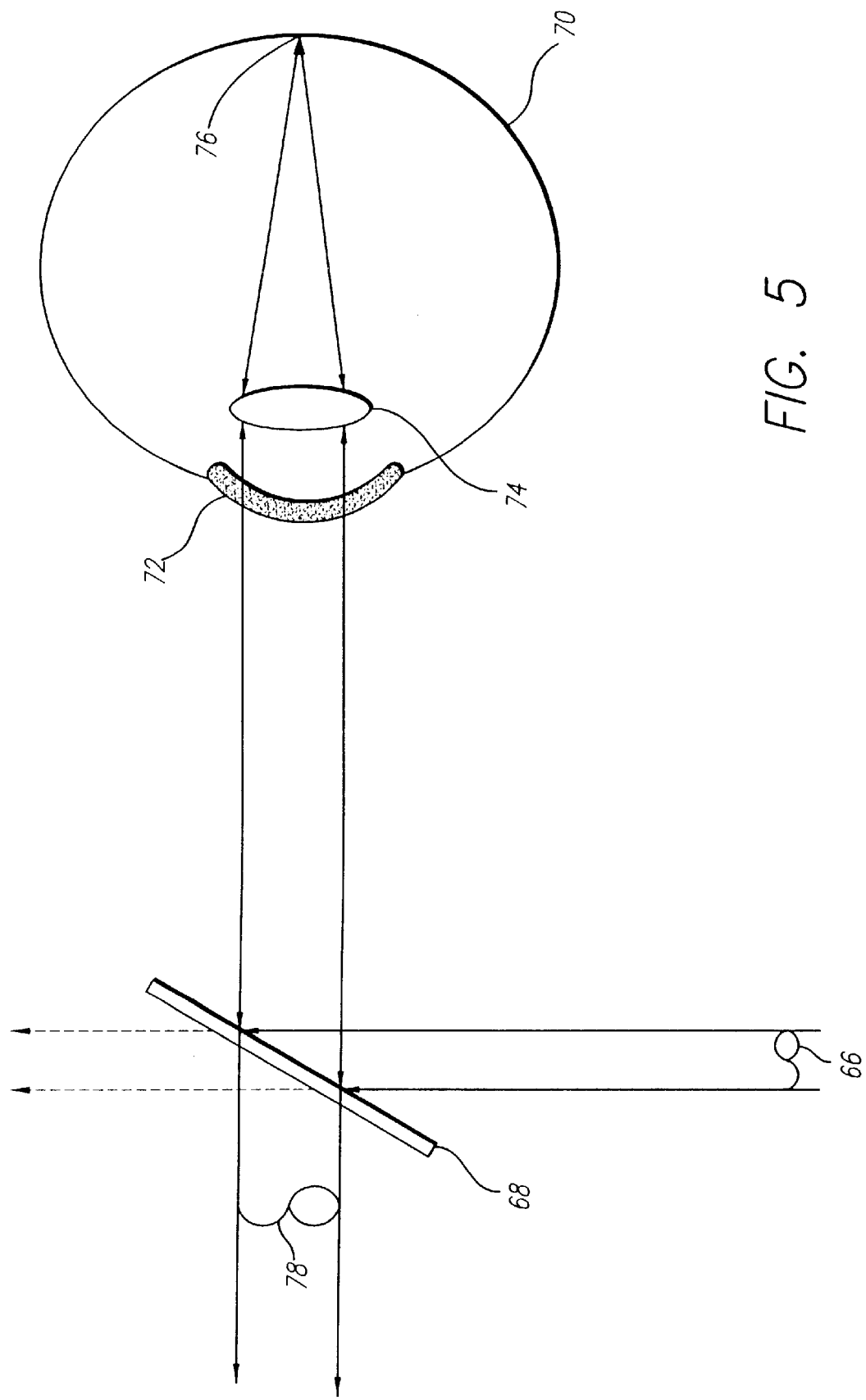
FIG. 5 is a diagram of the light path in the refractor operation of the ocular biometer.

This optical path of the accommodation measuring device or refractor, that measures the optical power of the eye, is shown in FIG. 5. A collimated beam 66 reflects from aperture sharing element 68 and is directed into the eye 70 passing through the cornea 72, the lens 74 and onto the retina 76. It then is scattered by the retinal structure and the generated wavefronts are propagated out of the eye 70 and this time passes through aperture sharing element 68 on its way 78 to the wavefront sensor.

Figure 6:
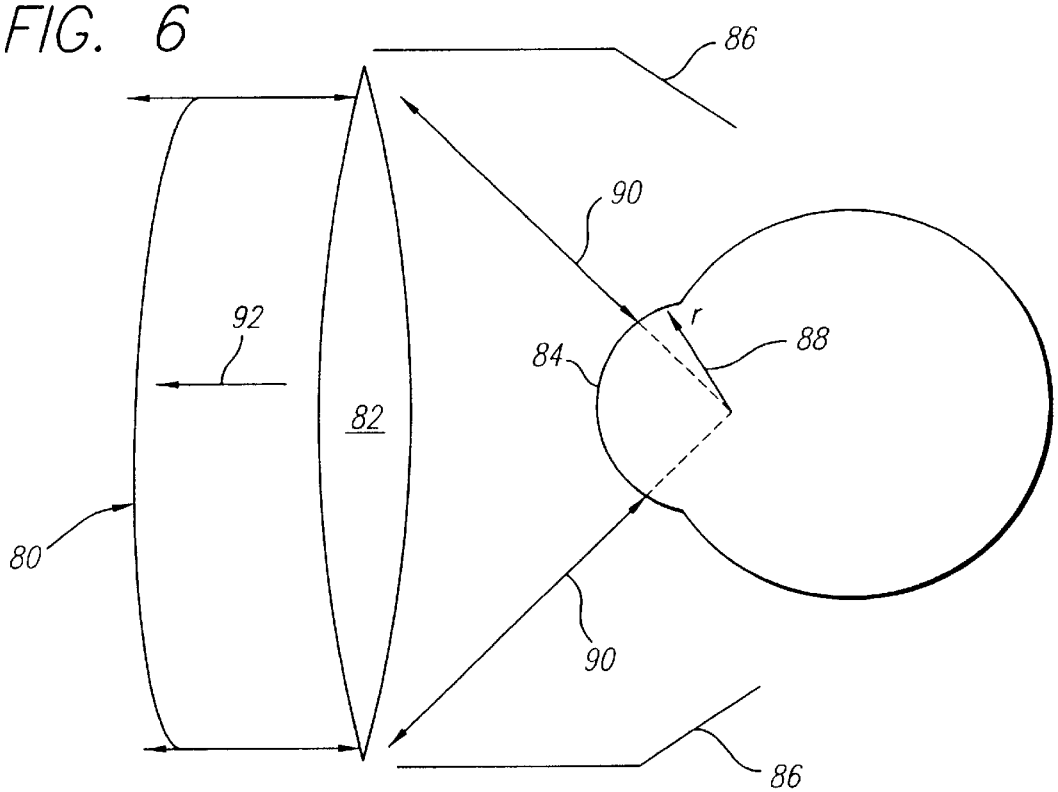
FIG. 6 is a schematic which shows the use of the null lens in the corneal shape and topograph measurement.

In order to provide topographical measurements of the cornea of the eye, there is needed a light source producing radiation in the wide spectral band. In FIG. 6 light 80 is from a radiation source. Light beam 80 is collimated so that when it is refracted through a nulling lens 82, light 80 is directed toward and approximately normal to the corneal surface 84. A support 86, such as an eye cup or eye piece, is used to position the eye so that the focus of null lens 82 is very near the center of curvature 88 of cornea 84. The convergent light 90 is then reflected by the cornea 84. Light reflected from the corneal epithelial surfaces is directed back through nulling lens 82 to produce a wavefront 92 that can be analyzed with results that are accurate measurements of the global surface.

Figure 7:
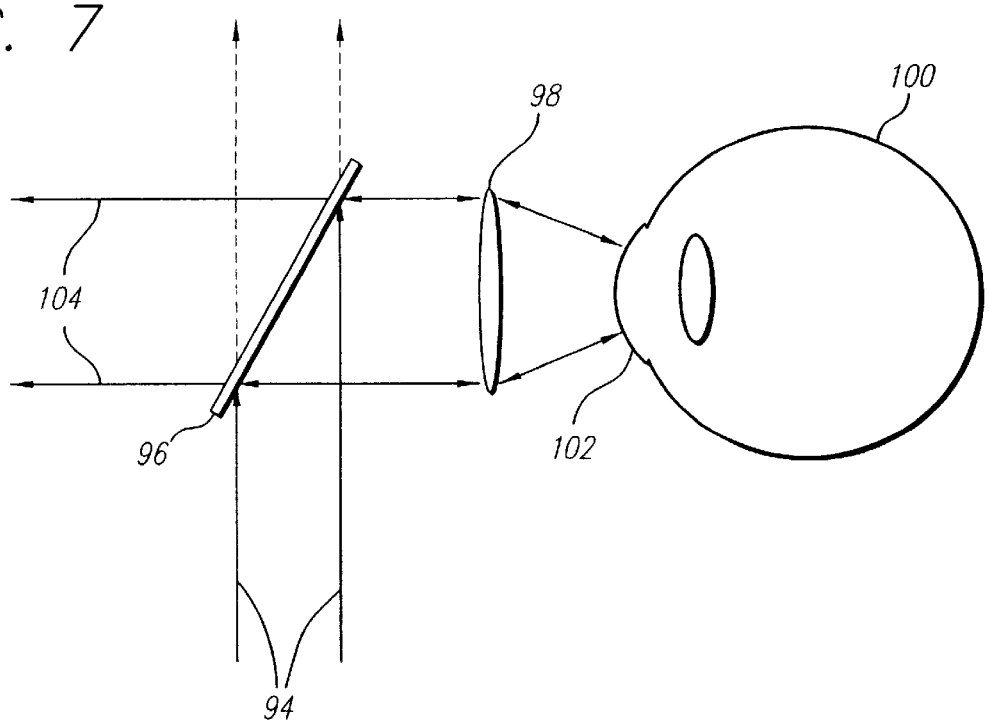
FIG. 7 is an optical schematic of the wavefront sensor in the corneal shape and topography measurement.

The optical path of a corneal mapper or keratopographer is shown in FIG. 7. A collimated beam 94 reflects from aperture sharing element 96 and is directed toward nulling lens 98 and onto the eye 100 and the cornea 102. It then is reflected by the corneal structure and the generated wavefront is propagated back through nulling lens 98 and this time passes through aperture sharing element 96 on its way 104 to the wavefront sensor.

Figure 8:
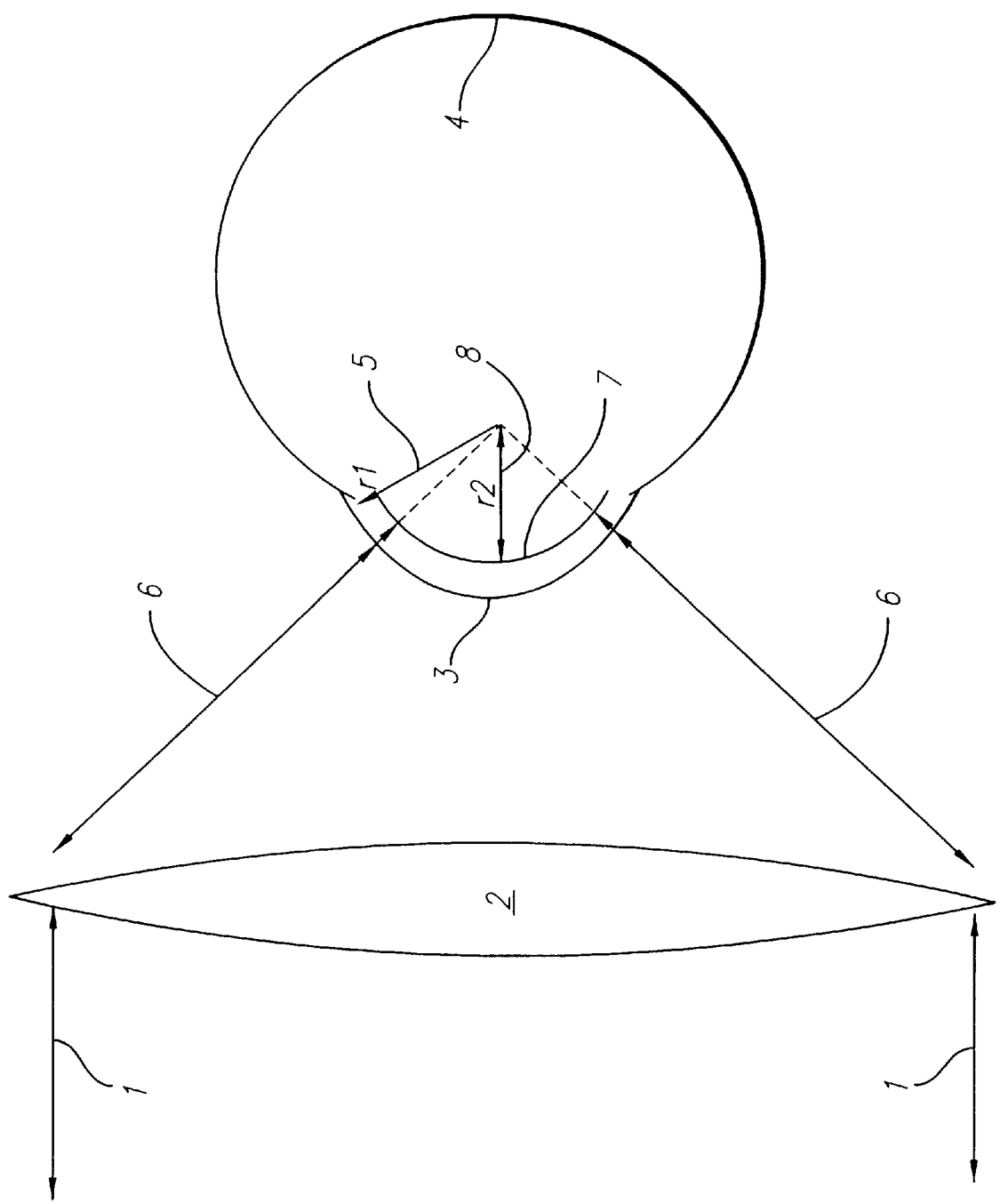
FIG. 8 is an optical schematic of the pachymeter for the measurement of the thickness of the cornea.

Making use of the spectral reflection characteristics of the cornea is illustrated in FIG. 8. The ocular biometer can measure two surfaces simultaneously and thus, in this case, measure the thickness or depth of the cornea at all locations. A schematic of the optical configuration of a pachymeter is shown in FIG. 8. Two different spectral regions or polarizations of illumination 106 are incident on nulling lens 108 from the left. They converge on the corneal surface 110 whereupon one of the spectral or polarized components of the incident will reflect. The other spectral or polarization component of the incident light will reflect from endothelial corneal surface 112. The two reflected wavefronts shown as 114 are refracted by nulling lens 108 and become wavefronts 116 to be analyzed by the wavefront sensor. The left most vertex of nulling lens 108 is the point at which the wavefront 116 in analyzed in FIG. 3. The resulting measurements are then the epithelial radius of curvature 118 $r_1$ and the endothelial surface radius of curvature 120 $r_2$. Both are measured with respect to the same center of curvature. Thus, the thickness of the cornea is determined by subtraction at any axial or radial location.

Figure 9:
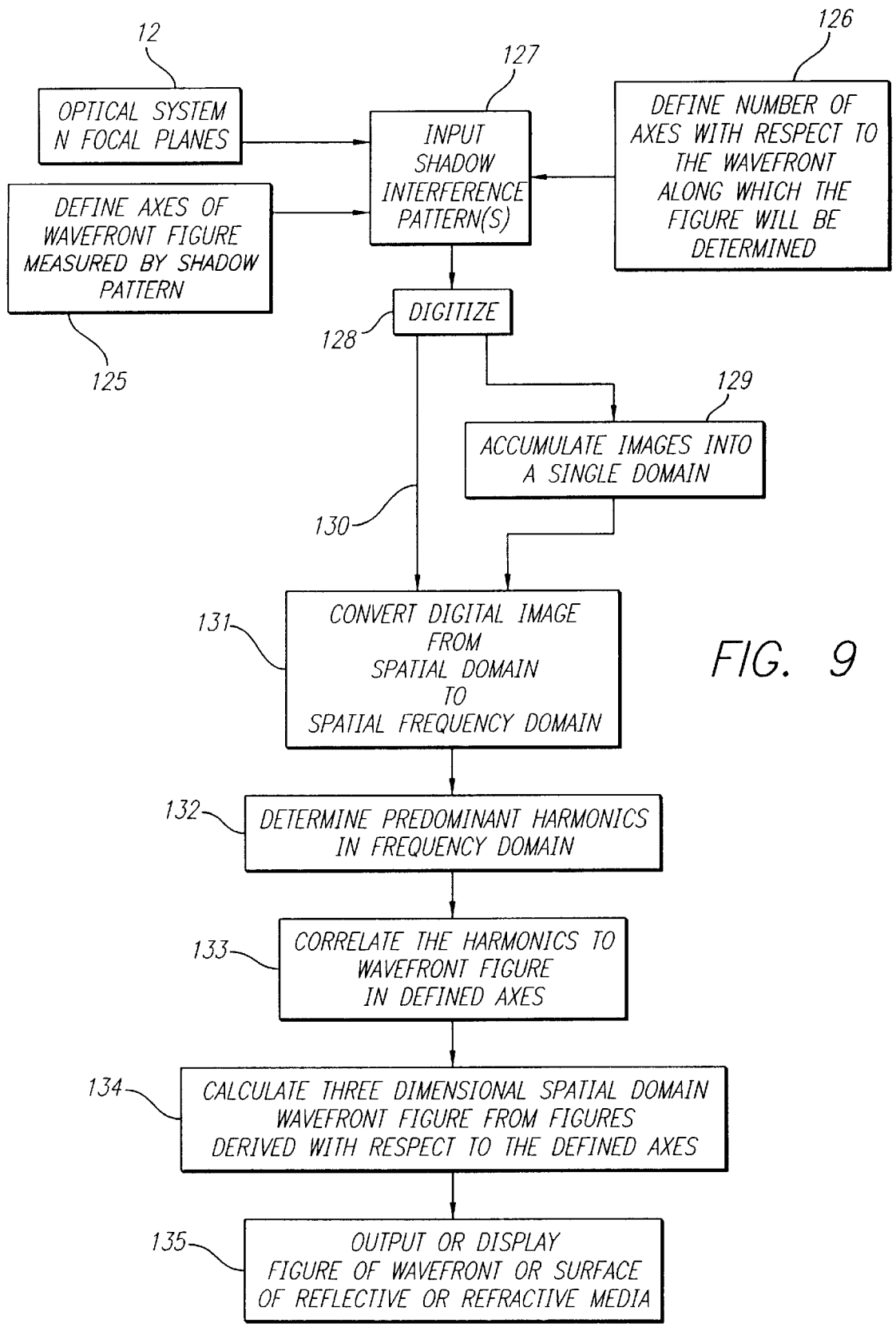
FIG. 9 is a logic flow diagram for the wavefront sensor data analysis algorithm.

The algorithm by which the wavefront is analyzed is shown in FIG. 9. The parameters that are put into the system are the number of axes 125, 126 along which the wavefront is to be analyzed and their orientation (definition), the number of data collection mechanisms (i.e., focal planes 124) that are needed to collect the data. The shadow patterns are collected by the focal planes and digitized 128. In some applications a number of patterns 129 can be cumulated into a single domain and analyzed simultaneously. In other applications only one pattern or set of patterns can be analyzed at a time. Thus, the branch 130. Then mathematical techniques, such as the Fourier transform, are used to convert the spatial domain of the pattern to the spatial frequency domain 131. The predominant harmonics in the frequency domain are then filtered from the data 132. These represent the figure (shape) of the wavefront in the defined axes. The "figure" is any spatial mode that is derived from the shadow pattern (e.g., spherical, coma, . . . through the $n^{th}$ order of spherical 133). Now in the spatial domaine the wavefront can be derived from these components. The wavefront is then interpreted as the optical power of an optical train such as the eye or the shape of a surface such as the cornea 134. The data is then sent to its respective system elements, FIG. 10 or FIG. 11, or output as data 135.

Figure 10:
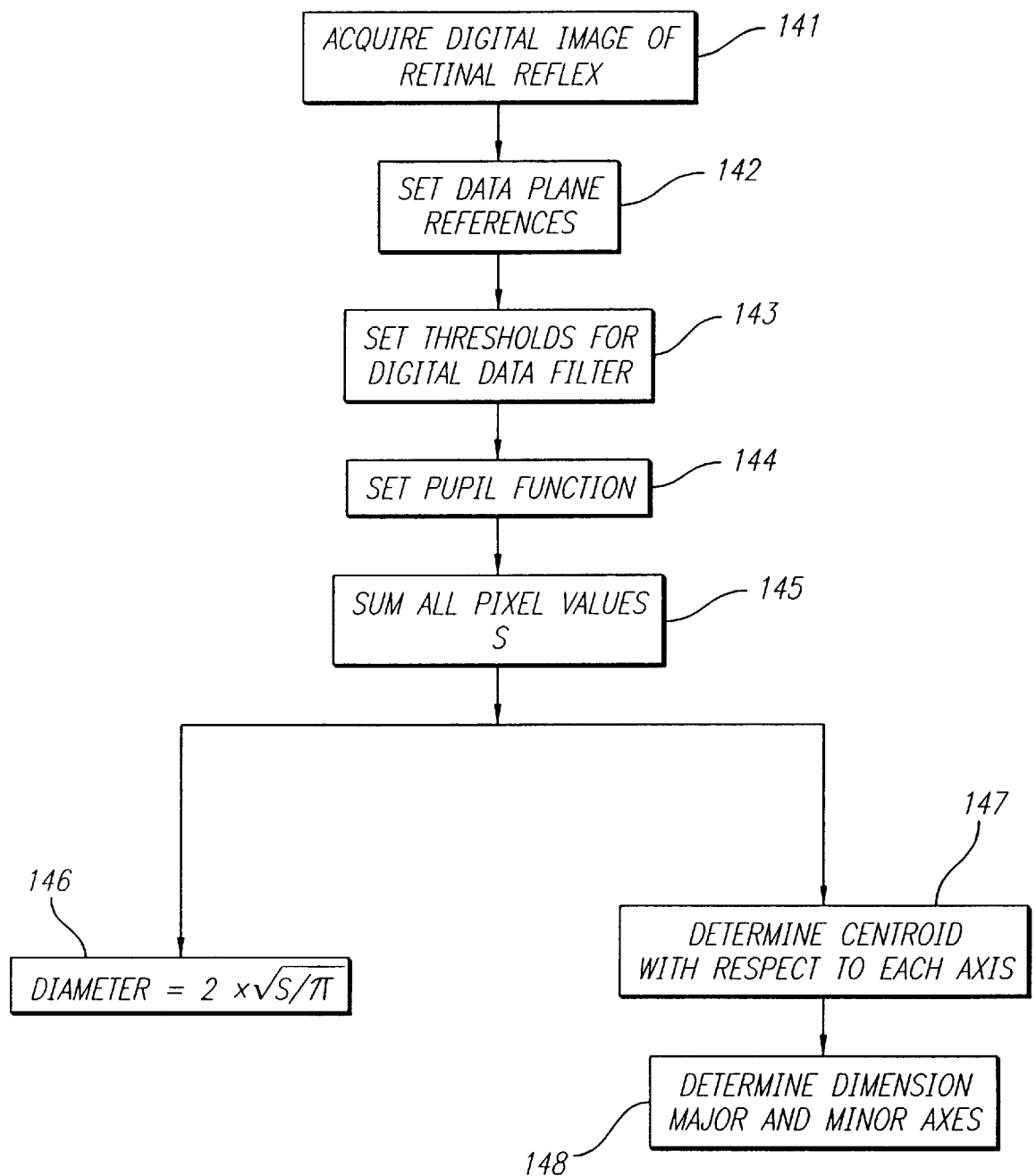
FIG. 10 is the logic flow diagram for the pupillometry analysis.
Figure 11:
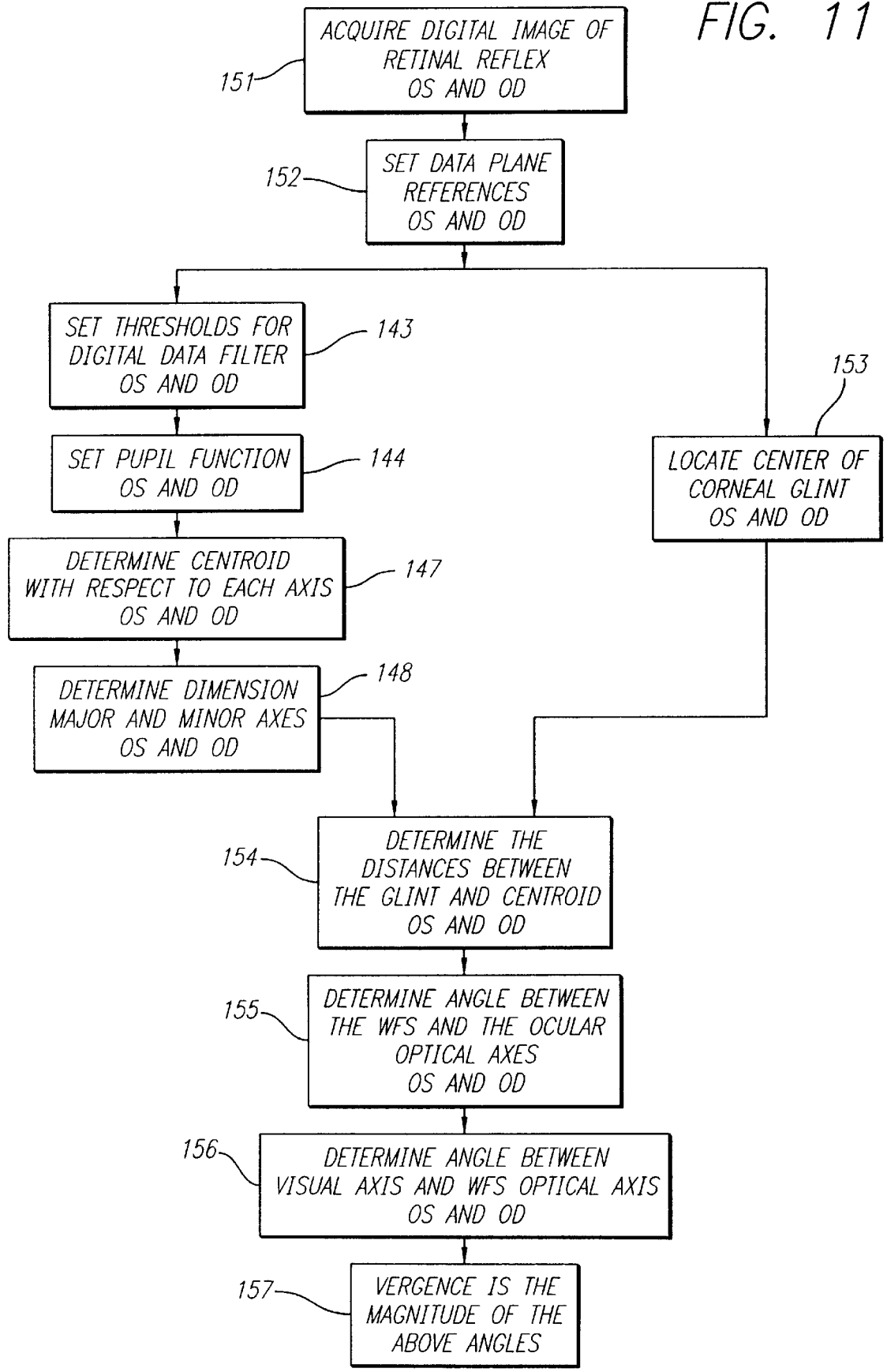
FIG. 11 is the logic flow diagram for the eye tracking analysis.

One of the functions of the ocular biometer is the measurement of the size of the ocular pupil. The algorithm charted in FIG. 10 is the same for both eyes and thus only one is shown. The data is collected and digitized as in FIG. 9, 141. Spatial coordinates are important in this analysis 142, thus reference coordinates must be defined. Then the data is conditioned by using data thresholds 143. That is, all data below a defined level is given a fixed value such as "0" (zero) and all data above another threshold is given another fixed value such a "1". Now the pupil functions set, i.e., either "0" or "1", 144. All pixels (or data cells) are then added together and normalized by the upper value (i.e., 1 in this example). Knowing the object space dimensions of the pixels, the area of the pupil is now known 145. Its diameter can be determined in two ways. If just knowing the average diameter is desired, then using the area of a circle is used to derive the diameter 146. If dimensions of certain axes are required then centroiding 147 and moments techniques are used 148.

The ocular biometer can be used to track the eyes and determine the vergence of the two eyes (i.e., where the lines-of-sight of the two eyes converge). The algorithm for this analysis is charted FIG. 11. OS and OD in the figure are the left eye and right eye respectively. Thus, "OS and OD" is used to indicate that the function is performed on the data from the two eyes simultaneously or in series. The data is then combined at the last function to obtain the vergence of the eyes. Again the data is collected 151, digitized and provided reference coordinates 152. Two sets of data points are now needed: (1) the centroids (geometric center) of the pupils as seen by the wavefront sensor (WFS), and (2) the location of the corneal glints 153 as imaged by the WFS's. The distances between each glint and the centroid 154 provides the look angle of the optical axis of the eye with respect to the optical axis of the WFS 155. These angles must then be adjusted for the differences between the optical axes of the eyes and the visual axes 156. These are then the gaze angle of the eyes. With positive angle being the nasal directions and negative angle being the temporal directions. Now the vergence is the magnitude of the sum of the two angles 157.

Figure 12:
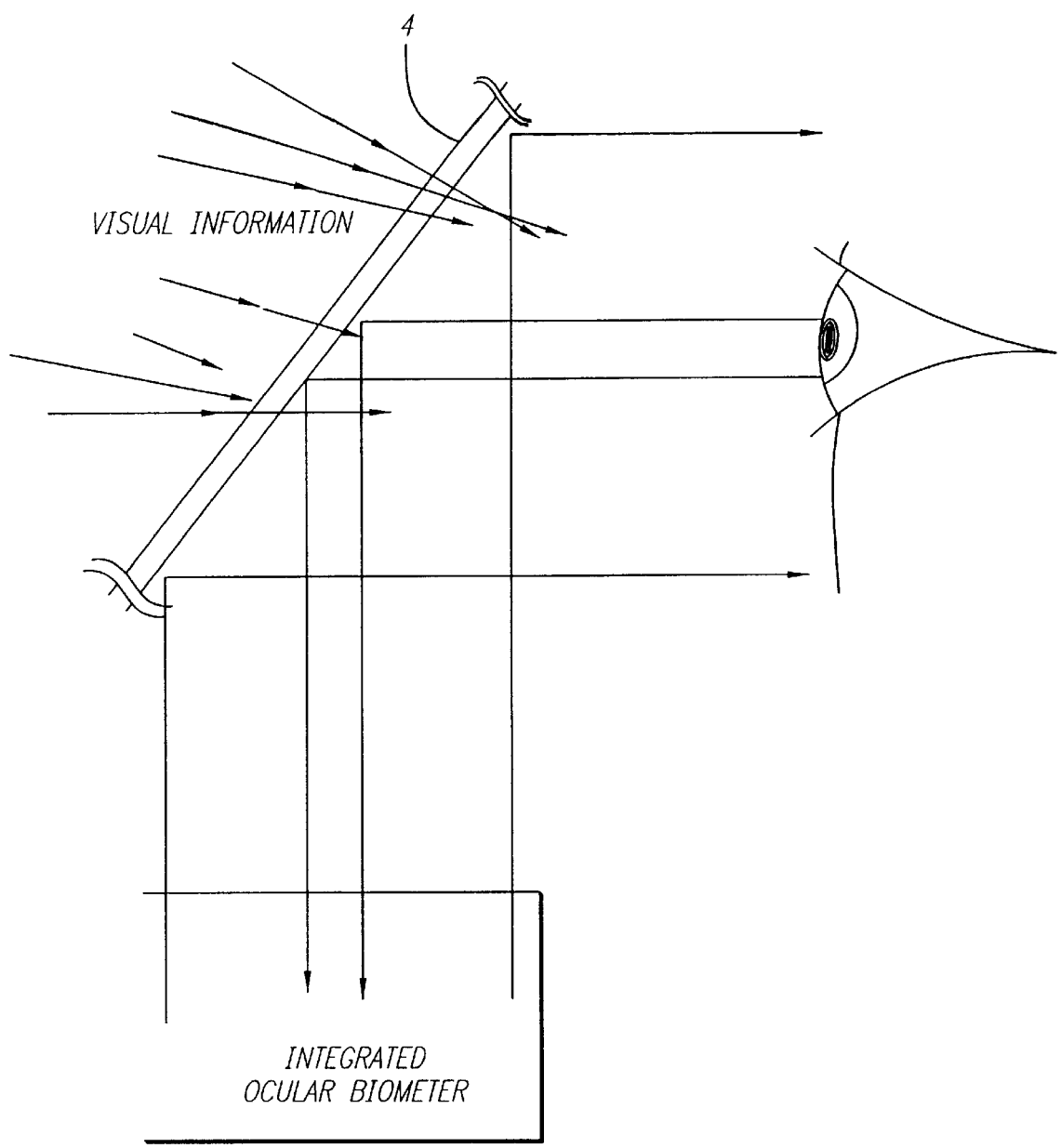
FIG. 12 is the human interface configuration with the ocular biometer and the real world.

A generic application of the ocular biometer is to monitor the ocular response in "life" scenario such as a automobile, truck, aircraft, spacecraft, work environment, etc. The ocular biometer, i.e., illumination source and wavefront sensor, must be integrated into the environment. However, the aperture sharing element 4 in FIG. 1 and FIG. 2 must allow the subject to view the environment. In FIG. 12 a generic configuration is illustrated where 4 is the aperture sharing element.

When both eyes are tracked, ocular vergence can be determined. Thus, a subsystem of the mechanism embodied in this application can be used: as a strabismometer, also known as ophthalmotropometer and strabometer for measurement of the vergent visual axes of the eyes; in Helmet Mounted Display (HMD) systems for fine pointing and tracking mechanisms; as a mental alertness indicator that is characterized by eye motion (sporadic or intentioned) used to detect falling asleep, drug usage or alcohol usage; video games where eye motion is an interaction with the game; and in research where eye motion is a parameter.

The system as indicated operates in a closed loop to effect optical measurements and also to determine the degree of corrective treatment that is necessary for the optical element. When the optical treatment is effected, the closed loop can provide different refractive signals and this can be adapted so that ultimately the optical conditions are rectified.

The ocular biometer system herein described requires no patient conscious feed-back. Thus, an objective binocular refraction can be performed. The corneal topography measurement requires no patient feedback. Therefore, all of the parameters of the patient's visual characteristics can be measured simultaneously in a binocular mode.

Corneal global topography is a mechanism needed to sample (i.e., make measurements from) the entire surface of the cornea. By combining ocular spectral reflectance information with wavefront sensing technology, the corneal surface topography is precisely and continuously measured. Such measurements will provide precise biometrics in order to fit contact lenses and to analyze the cornea for refractive surgical or therapeutic procedures.

The technique used in the keratometric method permits the dynamics of the eye to be tracked, i.e., an eye tracking sensor, as well as provide strabismus measurements. This can qualify eye motion or quantify it to 200 micro-radians (or, 0.01 degree).

This technique is useful in ophthalmic surgery, refractive surgical and therapeutic procedures, pointing and tracking in helmet mounted display systems, virtual reality systems, sensors to determine if a person is falling asleep (e.g., automobile sleep alarms), mental acuity tests (e.g., alcohol and drug tests), and video games in which eye tracking would be used as the interaction with the game.

Automatic, binocular or monocular refractive measurements of the vision of subject patients without causing eye strain or requiring verbal response are possible. Contact lens or spectacle lens prescriptions will be provided automatically as well as prescribed refractive surgical or tissue therapeutical procedures.

Precise topographies of the corneal surface, to be used in contact lens fitting, analysis of corneal scaring and lesions, ophthalmic research, and refractive surgical and tissue therapeutical procedures can be accomplished.

Many more examples and applications of the invention exist, each differing from the other in matters of detail only. The invention is to be considered limited only by the following claims.

I claim:

1. Apparatus for measuring characteristics of the eye compromising:
    (a) means for generating an optical wavefront;
    (b) means to transmit the optical wavefront to the eye, the wavefront reflecting from various surfaces of the eye;
    (c) baffle means for removal of optical wavefront noise;
    (d) one or more reticle means through which the reflected optical wavefront is passed to cast a shadow pattern;
    (e) means for directing the shadow pattern towards a screen; and
    (f) means for analyzing the shadow pattern on the screen to produce measurement data of the characteristics of the wavefront, thereby providing measurement characteristics of the eye.

2. The apparatus of claim 1 wherein the analyzing means compromises computation means for removal of data processing noise.

3. The apparatus of claim 1 further comprising means for generating a collimated beam of a predetermined wavelength to generate the optical wavefront.

4. The apparatus of claim 3 further comprising means to generate a collimated beam with a wavelength of from 780 to 900 nanometers.

5. The apparatus of claim 4 further comprising means to generate a collimated beam with a wavelength of about 840 nanometers and means to direct the beam onto the retinal surface of an eye.

6. The apparatus of claim 1 wherein the means to generate the optical wavefront is a light source with a wavelength of from 780 to 900 nanometers.

7. The apparatus of claim 1 further comprising means for tracking relative movements of the eye in any one or all of three dimensions.

8. Apparatus for measuring the characteristics of the eye comprising:
    (a) an illumination source to create an optical wavefront;
    (b) one or more aperture sharing elements for transmitting the optical wavefront to the eye, the wavefront reflecting from various surfaces of the eye;
    (c) a relay lens arrangement for focusing the wavefront reflected from the eye;
    (d) a baffle to eliminate noise;
    (e) one or more reticles through which the reflected optical wavefront is passed to cast a shadow pattern;

(f) a screen onto which the shadow pattern is directed;

(g) a camera to image the shadow pattern on the screen;

(h) a computer to analyze the information generated by the shadow pattern.

9. The apparatus of claim 8 further comprising means for generating a collimated beam of a predetermined wavelength to generate the optical wavefront.

10. The apparatus of claim 9 further comprising means to generate a collimated beam with a wavelength of from 780 to 900 nanometers.

11. The apparatus of claim 10 further comprising means to generate a collimated beam with a wavelength of about 840 nanometers and means to direct the beam onto the retinal surface of an eye.

12. The apparatus of claim 8 wherein the means to generate the optical wavefront is a light source with a wavelength of from 780 to 900 nanometers.

13. The apparatus of claim 8 further comprising means for tracking relative movements of the eye in any one or all of three dimensions.

14. A method for measuring characteristics of the eye compromising:

(a) generating an optical wavefront;

(b) transmitting the optical wavefront to the eye, the wavefront reflecting from various surfaces of the eye;

(c) passing the wavefront through a baffle for removal of optical wavefront noise;

(d) passing the reflected optical wavefront through one or more reticles to cast a shadow pattern;

(e) directing the shadow pattern towards a screen; and (f) analyzing the shadow pattern on the screen to produce measurement data of the characteristics of the wavefront, thereby providing measurement characteristics of the eye.

15. The method of claim 14 comprising removing data processing noise in the analysis.

16. The method of claim 14 comprising generating a collimated beam of a predetermined wavelength to generate the optical wavefront.

17. The method of claim 16 comprising generating a collimated beam with a wavelength of from 780 to 900 nanometers.

18. The method of claim 17 comprising generating a collimated beam with a wavelength of about 840 nanometers and directing the beam onto the retinal surface of an eye.

19. The method of claim 14 comprising generating the optical wavefront using a light source with a wavelength of from 780 to 900 nanometers.

20. The method of claim 14 comprising tracking relative movements of the eye in any one or all of three dimensions.

21. A method for measuring the characteristics of the eye comprising:

(a) creating an optical wavefront;

(b) passing the wavefront through one or more aperture sharing elements;

(c) passing the wavefront through a baffle for removal of optical wavefront noise;

(d) transmitting the optical wavefront to the eye, the wavefront reflecting from various surfaces of the eye;

(e) focusing the wavefront reflected from the eye;

(f) passing the wavefront through one or more reticles to cast a shadow pattern;

(g) directing the shadow pattern onto a screen;

(h) imaging the shadow pattern on the screen with a camera connected to computing means;

(i) analyzing the information imaged on the camera.

22. The method of claim 21 compromises removing data processing noise by the use of analyzing means.

23. The method of claim 21 comprising generating a collimated beam of a predetermined wavelength to generate the optical wavefront.

24. The method of claim 23 comprising generating a collimated beam with a wavelength of from 780 to 900 nanometers.

25. The method of claim 24 comprising generating a collimated beam with a wavelength of about 840 nanometers and directing the beam onto the retinal surface of the eye.

26. The method of claim 21 comprising generating the optical wavefront using a light source with a wavelength of from 780 to 900 nanometers.

27. The method of claim 21 tracking relative movements of the eye in any one or all of three dimensions.

28. A method for measuring a predetermined characteristic of the eye comprising:

(a) generating a collimated light beam;

(b) directing the beam into the eye wherein the beam is reflected from the eye;

(c) directing the reflected beam through a first reticle to develop a shadow pattern;

(d) directing the shadow pattern through a second reticle to develop a moire pattern; and (e) analyzing the moire pattern to produce measurement data of the eye.

29. The method of claim 28 comprising removal of noise and creating a substantially noise-free moire pattern thereby to provide measurement data of the eye.

30. A method for measuring the refractive characteristics of the eye comprising:

(a) creating an optical wavefront;

(b) passing the wavefront through one or more aperture sharing elements;

(c) directing the optical wavefront to the retinal surface of the eye, the wavefront reflecting from the retinal surface of the eye;

(d) focusing the wavefront reflected from the eye;

(e) passing the wavefront through a baffle for removal of optical wavefront noise;

(f) reforming the wavefront;

(g) passing the wavefront through one or more reticles to cast a shadow pattern;

(f) directing the shadow pattern onto a screen;

(g) imaging the shadow pattern on the screen with a camera connected to computing means;

(h) analyzing the information recorded by the camera.

31. A method for measuring the topographic characteristics of corneal elements of the eye comprising:

(a) creating an optical wavefront;

(b) passing the wavefront through one or more aperture sharing elements;

(c) passing the wavefront through a nulling lens so that the focus is near the center of curvature of the cornea;

(d) directing the optical wavefront to the epithelial surface of the eye, the wavefront reflecting from the epithelial surface of the eye;

(e) passing the wavefront through one or more reticles to cast a shadow pattern;

(f) directing the shadow pattern onto a screen;

(g) imaging the shadow pattern on the screen with a camera connected to computing means;

(h) analyzing the information recorded by the camera.

32. A method for measuring the the topography of the endothelial surface of the eye comprising:

(a) creating an optical wavefront;

(b) passing the wavefront through one or more aperture sharing elements;

(c) directing the optical wavefront globally to the endothelial surface of the eye, the wavefront reflecting from the endothelial surface of the eye;

(d) focusing the wavefront reflected from the eye;

(e) spatial filtering the focused wavefront;

(f) reforming the wavefront;

(g) passing the wavefront through one or more reticles to cast a shadow pattern;

(h) directing the shadow pattern onto a screen;

(i) imaging the shadow pattern on the screen with a camera connected to computing means;

(j) analyzing the information recorded by the camera.

33. A method for measuring the thickness of the cornea of the eye comprising:

(a) creating one or more optical wavefronts;

(b) passing the wavefronts through one or more aperture sharing elements;

(c) directing the optical wavefronts to both the epithelial and endothelial surfaces of the eye, the wavefronts reflecting from both said surfaces;

(d) discriminating the reflected wavefronts by spectral or polarization characteristics;

(e) passing the wavefront through one or more reticles to cast a shadow pattern;

(f) directing the shadow pattern onto a screen;

(g) recording the shadow pattern on the screen with a camera connected to computing means;

(h) analyzing the information recorded by the camera.

34. A method for measuring the pupil of the eye comprising:

(a) creating an optical wavefront;

(b) passing the wavefront through one or more aperture sharing elements;

(c) directing the optical wavefront through the pupil of the eye to the retina, the wavefront reflecting from the retina of the eye;

(d) directing the illumintion onto a screen;

(i) imaging the shadow pattern on the screen with a camera connected to computing means;

(j) analyzing the information recorded by the camera.

35. A method for measuring the optical refractive power of the eye comprising:

(a) creating an optical wavefront;

(b) passing the wavefront through one or more aperture sharing elements;

(c) directing the optical wavefront to the retina of the eye, the wavefront relecting from the retina of the eye;

(d) focusing the wavefront reflected from the retina of the eye;

(e) spatial filtering the focused wavefront;

(f) reforming the wavefront;

(g) passing the wavefront through one or more reticles to cast a shadow pattern;

(h) directing the shadow pattern onto a screen;

(i) imaging the shadow pattern on the screen with a camera connected to computing means;

(j) analyzing the information imaged on the camera to obtain the optical refractive power of the eye.

36. A method for measuring a spatially resolved refraction of the eye comprising:

(a) creating an optical wavefront;

(b) passing the wavefront through one or more aperture sharing elements;

(c) directing the optical wavefront to the retina of the eye, the wavefront reflecting from the retina of the eye;

(d) focusing the wavefront reflected from the eye;

(e) spatial filtering the focused wavefront;

(f) reforming the wavefront;

(g) passing the wavefront through one or more reticles to cast a shadow pattern;

(h) directing the shadow pattern onto a screen;

(i) recording the shadow pattern on the screen with a camera connected to computing means;

(j) analyzing a predetermined specific spatial or angular portion of the eye's field of view from the information recorded on the camera.

37. A method for measuring the direction of the line of sight of the eye comprising:

(a) creating an optical wavefront;

(b) passing the wavefront through one or more aperture sharing elements;

(c) directing the optical wavefront to the eye;

(d) imaging the reflected light from the eye at the vertex of the cornea;

(e) measuring the position of the glint of the eye;

(f) measuring the position of the centroid of the pupil of the eye;

(g) analyzing the measurement information.

38. The methods of claims 30, 31, 32, 33, 34, 35, 36 and 37 wherein the measurements are done binocularly, in both eyes simultaneously.

39. A method for measuring the vergence of the eyes comprising:

(a) creating an optical wavefront;

(b) passing the wavefront through one or more aperture sharing elements;

(c) directing the optical wavefront to both eyes;

(d) imaging the reflected light from the eye at the vertex of the cornea;

(e) measuring the position of the glint of both eyes;

(f) measuring the position of the centroid of the pupil of both eyes;

(g) analyzing the measurement information by comparing the line of sight of both eyes.

40. The methods of claims 30, 31, 32, 33, 34, 35, 36, 37 and 39 wherein the analysis comprises:

(c) digitizing the shadow patterns;

(d) accumulating the digital images into a single spatial domaine;

(e) converting the spacial domaine to a spatial frequency domaine;

(f) determining the predominant harmonics in the frequency domaine;

(g) correlating the predominant harmonics to the wavefront figure in defined axes;

(h) calculating a three dimensional optical domaine wavefront figure derived from the defined axes;

(i) analyzing the measurements of the wavefront figure.

41. A method for analyzing an optical wavefront comprising:

(a) generating shadow patterns from the optical wavefront;

(b) collecting the shadow patterns generated;

(c) digitizing the shadow patterns;

(d) accumulating the digital images into a single spatial domaine;

(e) converting the spacial domaine to a spatial frequency domaine;

(f) determining the predominant harmonics in the frequency domaine;

(g) correlating the predominant harmonics to the wavefront figure in defined axes;

(h) calculating a three dimensional optical domaine wavefront figure derived from the defined axes;

(i) analyzing the measurements of the wavefront figure.

42. A method for measuring the refractive characteristics of the eye comprising:

(a) creating an optical wavefront;

(b) passing the wavefront through one or more aperture sharing elements;

(c) directing the optical wavefront to the eye, the wavefront reflecting from the various surfaces of the eye;

(d) focusing the wavefront reflected from the eye;

(e) passing the wavefront through a baffle to eliminate noise;

(e) spatial filtering the wavefront to eliminate ambient noise;

(f) reforming the wavefront;

(g) passing the wavefront through one or more reticles to cast a shadow pattern;

(h) directing the shadow pattern onto a screen;

(i) recording the shadow pattern on the screen with a camera to convert the screen image to spatial digital data;

(j) converting the spatial digital data to spatial frequency data;

(k) determining the dominant spatial frequency;

(l) correlating the dominant spatial frequency to the spherical component along the corresponding axis of the wavefront;

(m) determining the figure of the entire wavefront with the figures of the component axes.

* * * * *